United States Patent [19]

Tomiyama et al.

[11] Patent Number: 5,527,815
[45] Date of Patent: Jun. 18, 1996

[54] CARBOXYMETHYLIDENECYCLOHEPT-IMIDAZOLE DERIVATIVES, METHOD OF MANUFACTURING THE SAME AND THERAPEUTIC AGENTS CONTAINING THESE COMPOUNDS

[75] Inventors: Tsuyoshi Tomiyama; Akira Tomiyama, both of Hanishina-gun; Takashi Yanagisawa, Kousyoku; Naoto Ueyama; Hiromi Baba, both of Ueda, all of Japan

[73] Assignee: Kotobuki Seiyaku Co., Ltd., Nagano-ken, Japan

[21] Appl. No.: 282,591

[22] Filed: Jul. 29, 1994

[30] Foreign Application Priority Data

Jul. 30, 1993 [JP] Japan .................................. 5-190153

[51] Int. Cl.$^6$ ..................... C07D 403/10; A61K 31/415
[52] U.S. Cl. ........................................... 514/381; 548/253
[58] Field of Search ................................ 548/253, 302.7; 514/381

[56] References Cited

U.S. PATENT DOCUMENTS

| 4,675,335 | 6/1987 | Baker et al. | 514/381 |
| 4,870,186 | 9/1989 | Ardrich et al. | 548/215 |
| 5,104,891 | 4/1992 | Bovy et al. | 514/381 |
| 5,128,356 | 7/1992 | Naka et al. | 514/381 |
| 5,294,631 | 3/1994 | Franz et al. | 514/381 |

FOREIGN PATENT DOCUMENTS

| 0147177 | 3/1985 | European Pat. Off. . |
| 0401030 | 12/1990 | European Pat. Off. . |
| 432737 | 6/1991 | European Pat. Off. . |
| 459136 | 12/1991 | European Pat. Off. . |

OTHER PUBLICATIONS

Journal of Medicinal Chemistry, vol. 36, No. 12, 11 Jun. 1993, Washington pp. 1772–1784, K. Kubo, et al. "Nonpeptide Angiotensin II Receptor Antagonists. Synthesis and Biological Activity of Benzimidazoles".

Grant, R. et al. *Grant & Hackh's Chemical Dictionary* (McGraw—Hill, New York), pp. 366 and 368 (1987).

Journal of Medicinal Chemistry, vol. 36, No. 1, 8 Janvier 1993, Washington pp. 101–110, P. R. Bovy, et al. "Nonpeptide Angiotensin II Antagonists: N–Phenyl–1H–pyrrole Derivatives Are Angiotensin II Receptor Antagonists".

Journal of Medicinal Chemistry, vol. 35, No. 21, 16 Oct. 1992, Washington, pp. 3858–3872, R. M. Keenan, et al. "Imidazole–5–Acrylic Acids: Potent Nonpeptide Angiotensin II Receptor Antagonists Designed Using a Novel Peptide Pharmacophore Model".

Naoto Ueyama, et al., Bioorg. Med. Chem. Lett., vol. 4, No. 13, pp. 1637–1642, 1994. Publication month not provided.
Chemical Abstract 157466–64–4, Copyright 1994, American Chemical Society.
Chemical Abstract 157466–66–5, Copyright 1994, American Chemical Society.
Chemical Abstract 157466–67–6, Copyright 1994, American Chemical Society.
Chemical Abstract 157466–68–7, Copyright 1994, American Chemical Society.
Chemical Abstract 157466–69–8, Copyright 1994, American Chemical Society.
Chemical Abstract 157466–49–4, Copyright 1994, American Chemical Society.
Chemical Abstract 157466–48–3, Copyright 1994, American Chemical Society.
Chemical Abstract 157466–47–2, Copyright 1994, American Chemical Society.
Chemical Abstract 157466–46–1, Copyright 1994, American Chemical Society.
Chemical Abstract 157466–45–0, Copyright 1994, American Chemical Society.
Chemical Abstract 157466–27–8, Copyright 1994, American Chemical Society.
Chemical Abstract 157466–26–7, Copyright 1994, American Chemical Society.

(List continued on next page.)

*Primary Examiner*—Cecilia Tsang
*Assistant Examiner*—King Lit Wong
*Attorney, Agent, or Firm*—Sherman and Shalloway

[57] ABSTRACT

New therapeutic agent of carboxymethylidenecycloheptimidazole derivatives and method for the manufacture thereof are disclosed, which are represented by the following formula or its alkali addition salts

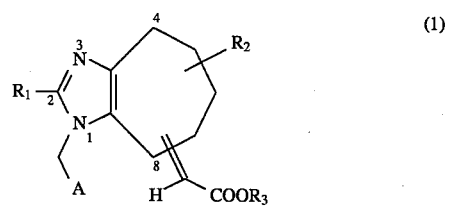

(wherein $R_1$ represents a lower alkyl; $R_2$ represents H or isopropyl group; $R_3$ represent H, a lower alkyl or —C(CH$_3$)H—OCOOR$_4$ (R$_4$ is a lower alkyl or cyclohexyl) and =CHCOOR$_3$ is substituted group at 4 or 8 position; A represents

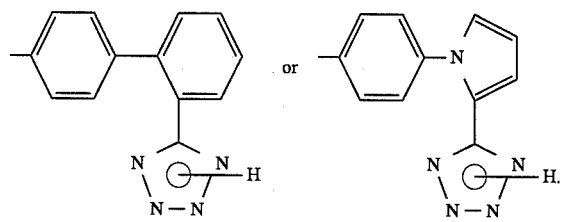

These compounds are useful as anti-hypertensive, anti-congestive heart failure agents and intraocular pressure lowering agents.

22 Claims, No Drawings

OTHER PUBLICATIONS

March., J., *Advanced Organic Chemistry Reactions, Mechanisms, and Structure* New York, John Wiley (1992), p. 946.

van der Veen, R. H. et al., Canadian Journal of Chemistry, vol. 62 (1984), pp. 2202–2205.

Carey, F. A. et al., *Advanced Organic Chemistry,* Part B New York, Plenum (1990), p. 100.

Evans, B. E. et al., Journal of Medicinal Chemistry, vol. 35 (1992), pp. 3919–3927.

Garrison, J. C. et al. "Renin and Angiotensin" in: Gilman, A. G. et al., *Goodman and Gilman's The Pharmacological Basis of Therapeutics.* New York, Pergamon (1990), pp. 755, 756, and 761.

CARBOXYMETHYLIDENECYCLOHEPT-IMIDAZOLE DERIVATIVES, METHOD OF MANUFACTURING THE SAME AND THERAPEUTIC AGENTS CONTAINING THESE COMPOUNDS

BACKGROUND OF THE INVENTION

1. Field of the Invention

This invention relates to a novel carboxymethylidenecycloheptimidazole derivatives and alkali addition salts, a method of their synthesis and their use as potent antihypertensive, anticongestive heart failure agents and intraocular pressure lowering agents.

2. Description of the Prior Art

Many therapeutic agents have been developed as antihypertensive, anticongestive heart failure agents and intraocular pressure lowering agents. One approach is to use angiotensin converting enzyme (ACE) inhibitors. In the renin-angiotensin system (RAS), angiotensinogen is hydrolyzed to angiotensin I (AI) by the renin, and AI is converted to the final product, angiotensin II (AII), which have a strong vasoconstrictive action. It has been well known that AII is related to cause hypertension and congestive heart failure. These ACE inhibitors are currently used to inhibit the formation of AII. Another approach is to block the action of AII at the AII receptor level and several peptide-AII receptor antagonists are reported. However these AII receptor antagonists have a poor oral activity. From this reason, non-peptide receptor antagonist having good oral activity has been required. Recently, several types of non-peptide compounds are proposed as angiotensin II receptor antagonists. For example, Japanese Patent Publications 1-117876 and 3-2169 describe imidazole derivatives, and Japanese Patent Publications 3-95181, 3-5480 and 3-5464 describe imidazopyridine derivatives. Furthermore, we have proposed the cycloheptimidazole derivatives (Japanese Patent application 4-131142).

3. Problems to be Solved by the Invention

A primary object of the present invention is to find a new carboxymethylidenecycloheptimidazole derivatives having an orally active angiotensin II receptor antagonist and provide a treatment agent for hypertension and congestive heart failure or an intraocular pressure reducing agent and a production method thereof.

SUMMARY OF THE INVENTION

The principal object of the present invention is the provision of compounds having Angiotensin II receptor antagonistic activities.

Another object of the present invention is the provision of pharmaceutical compositions useful as anti-hypertensive, anti-congestive heart failure agents and intraocular pressure lowering agents.

Still another object of the present invention is the provision of new carboxymethylidenecycloheptimidazole derivatives and a method for the manufacture thereof.

These and other objects of the invention will become apparent from the description that follows.

DETAILED DESCRIPTION OF THE INVENTION

This invention relates to new carboxymethylidenecycloheptimidazole derivatives and their alkali addition salts (Na, K, Ca and Mg salts etc.) and a method of their synthesis and use as potent anti-hypertensive, anti-congestive heart failure agents and intraocular pressure lowering agents.

The compounds of this invention are represented by the general formula (1)

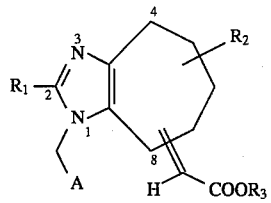

(wherein $R_1$ represents a lower alkyl group; $R_2$ represents a hydrogen or isopropyl group; $R_3$ represents a hydrogen, a lower alkyl group or

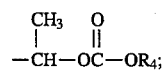

($R_4$ is a lower alkyl or cyclohexyl group);

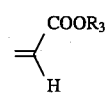

is substituted group at the 4 or 8 position; A is

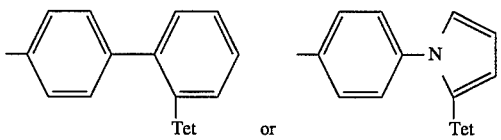

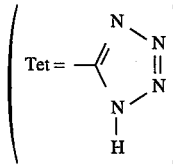

As used herein, lower alkyl includes from 1 to 6 carbon atoms.

The compounds as the general formula (1) possess a potent angiotensin II receptor antagonistic activities and they are regarded as therapeutically useful.

The compounds related to the general formula (1) are exemplified as follows:

(1) 2-Propyl-4-ethoxycarbonylmethylidene-1-[(2'-(1H-tetrazole-5-yl)biphenyl- 4-yl)methyl]-5,6,7,8-tetrahydro-cycloheptimidazole (Compound 1)

(2) 2-Methyl-8-ethoxycarbonylmethylidene-1-[(2'-(1H-tetrazole-5-yl)biphenyl- 4-yl)methyl]-4,5,6,7-tetrahydro-cycloheptimidazole (Compound 2)

(3) 2-Ethyl-8-ethoxycarbonylmethylidene-1-[(2'-(1H-tetrazole-5-yl)biphenyl- 4-yl)methyl]-4,5,6,7-tetrahydro-cycloheptimidazole (Compound 3)

(4) 2-Propyl-8-ethoxycarbonylmethylidene-1-[(2'-(1H-tetrazole-5-yl)biphenyl-4-yl)methyl]-4,5,6,7-tetrahydro-cycloheptimidazole (Compound 4)

(5) 2-Butyl-8-ethoxycarbonylmethylidene-1-[(2'-(1H-tetrazole-5-yl)biphenyl-4-yl)methyl]-4,5,6,7-tetrahydro-cycloheptimidazole (Compound 5)

(6) 2-Pentyl-8-ethoxycarbonylmethylidene-1-[(2'-(1H-tetrazole-5-yl)biphenyl-4-yl)methyl]-4,5,6,7-tetrahydro-cycloheptimidazole (Compound 6)

(7) 2-Ethyl-6-isopropyl-8-ethoxycarbonylmethylidene-1-[(2'-(1H-tetrazole- 5yl)biphenyl-4-yl)methyl]-4,5,6,7-tetrahydro-cycloheptimidazole (Compound 7)

(8) 2-Propyl-6-isopropyl-8-ethoxycarbonylmethylidene-1-[(2'-(1H-tetrazole-5-yl)biphenyl-4-yl)methyl]-4,5,6,7-tetrahydro-cycloheptimidazole (Compound 8)

(9) 2-Methyl-8-ethoxycarbonylmethylidene-1-[(4-(1H-pyrrole-2-(1H-tetrazole-5-yl)phenyl)methyl]-4,5,6,7-tetrahydro-cycloheptimidazole (Compound 9)

(10) 2-Ethyl-8-ethoxycarbonylmethylidene-1-[4-(1H-pyrrole-2-(1H-tetrazole-5-yl)phenyl)methyl]-4,5,6,7-tetrahydro-cycloheptimidazole (Compound 10)

(11) 2-Propyl-8-ethoxycarbonylmethylidene-1-[4-(1H-pyrrole-2-(1H-tetrazole-5-yl)phenyl)methyl]-4,5,6,7-tetrahydro-cycloheptimidazole (Compound 11)

(12) 2-Butyl-6-isopropyl-8-ethoxycarbonylmethylidene-1-[(2'-(1H-tetrazole-5-yl)biphenyl-4-yl)methyl]-4,5,6,7-tetrahydro-cycloheptimidazole (Compound 12)

(13) 2-Butyl-8-ethoxycarbonylmethylidene-1-[4-(1H-pyrrole-2-(1H-tetrazole-5-yl)phenyl)methyl]-4,5,6,7-tetrahydro-cycloheptimidazole (Compound 13)

(14) 2-Propyl-4-carboxymethylidene-1-[(2'-(1H-tetrazole-5-yl)biphenyl-4-yl)methyl]-5,6,7,8-tetrahydro-cycloheptimidazole (Compound 14)

(15) 2-Methyl-8-carboxymethylidene-1-[(2'-(1H-tetrazole-5-yl)biphenyl-4-yl)methyl]-4,5,6,7-tetrahydro-cycloheptimidazole (Compound 15)

(16) 2-Ethyl-8-carboxymethylidene-1-[(2'-(1H-tetrazole-5-yl)biphenyl-4-yl)methyl]-4,5,6,7-tetrahydro-cycloheptimidazole (Compound 16)

(17) 2-Propyl-8-carboxymethylidene-1-[(2'-(1H-tetrazole-5-yl)biphenyl-4-yl)methyl]-4,5,6,7-tetrahydro-cycloheptimidazole (Compound 17)

(18) 2-Butyl-8-carboxymethylidene-1-[(2'-(1H-tetrazole-5-yl)biphenyl-4-yl)methyl]-4,5,6,7-tetrahydro-cycloheptimidazole (Compound 18)

(19) 2-Pentyl-8-carboxymethylidene-1-[(2'-(1H-tetrazole-5-yl)biphenyl-4-yl)methyl]-4,5,6,7-tetrahydro-cycloheptimidazole (Compound 19)

(20) 2-Ethyl-6-isopropyl-8-carboxymethylidene-1-[(2'-(1H-tetrazole-5-yl)biphenyl-4-yl)methyl]-4,5,6,7-tetrahydro-cycloheptimidazole (Compound 20)

(21) 2-Propyl-6-isopropyl-8-carboxymethylidene-1-[(2'-(1H-tetrazole-5-yl)biphenyl-4-yl)methyl]-4,5,6,7-tetrahydro-cycloheptimidazole (Compound 21)

(22) 2-Methyl-8-carboxymethylidene-1-[4-(1H-pyrrole-2-(1H-tetrazole-5-yl)phenyl)methyl]-4,5,6,7-tetrahydro-cycloheptimidazole (Compound 22)

(23) 2-Ethyl-8-carboxymethylidene-1-[4-(1H-pyrrole-2-(1H-tetrazole-5-yl)phenyl)methyl]-4,5,6,7-tetrahydro-cycloheptimidazole (Compound 23)

(24) 2-Propyl-8-carboxymethylidene-1-[4-(1H-pyrrole-2-(1H-tetrazole-5-yl)phenyl)methyl]-4,5,6,7-tetrahydro-cycloheptimidazole (Compound 24)

(25) 2-Butyl-6-isopropyl-8-carboxymethylidene-1-[(2'-(1H-tetrazole-5-yl)biphenyl-4-yl)methyl]-4,5,6,7-tetrahydro-cycloheptimidazole (Compound 25)

(26) 2-Butyl-8-carboxymethylidene-1-[4-(1H-pyrrole-2-(1H-tetrazole-5-yl)phenyl)methyl]-4,5,6,7-tetrahydro-cycloheptimidazole (Compound 26)

(27) 2-Propyl-8-(1-ethoxycarbonyloxy)ethoxycarbonylmethylidene-1-[(2'-(1H-tetrazole-5-yl)-methyl]-4,5,6,7-tetrahydro-cycloheptimidazole (Compound 27)

(28) 2-Propyl-8-(1-cyclohexylcarbonyloxy)ethoxycarbonylmethylidene-1-[(2'-(1H-tetrazole-5-yl)biphenyl-4-yl)methyl]-4,5,6,7-tetrahydro-cycloheptimidazole (Compound 28)

(29) 2-Propyl-8-(1-isopropoxycarbonyloxy)ethoxycarbonylmethylidene-1-[(2'-(1H-tetrazole-5-yl)biphenyl-4-yl)methyl]-4,5,6,7-tetrahydro-cycloheptimidazole (Compound 29)

(30) 2-Ethyl-8-(1-isopropoxycarbonyloxy)ethoxycarbonylmethylidene-1-[(2'-(1H-tetrazole-5-yl)biphenyl-4-yl)methyl]-4,5,6,7-tetrahydro-cycloheptimidazole (Compound 30)

(31) 2-Ethyl-6-isopropyl-8-(1-isopropoxycarbonyloxy)-ethoxycarbonylmethylidene-1-[(2'-( 1H-tetrazole-5-yl)-biphenyl-4-yl)methyl]-4,5,6,7-tetrahydro cycloheptimidazole (Compound 31)

(32) 2-Ethyl-8-(1-isopropoxycarbonyloxy)ethoxycarbonylmethylidene-[4-(1H-pyrrole-2-(1H-tetrazole-5-yl)phenyl)methyl]-4,5,6,7-tetrahydro-cycloheptimidazole (Compound 32)

(33) 2-Propyl-6-isopropyl-8-(1-isopropoxycarbonyloxy)-ethoxycarbonylmethylidene-1-[(2'-( 1H-tetrazole-5-yl)-biphenyl-4-yl)methyl]-4,5,6,7-tetrahydro-cycloheptimidazole (Compound 33)

(34) 2-Butyl-6-isopropyl-8-(1-isopropoxycarbonyloxy)-ethoxycarbonylmethylidene-1-[( 2'-(1H-tetrazole-5-yl)-biphenyl-4-yl)methyl]-4,5,6,7-tetrahydro-cycloheptimidazole (Compound 34)

(35) 2-Ethyl-8-(1-cyclohexylcarbonyloxy)ethoxycarbonylmethylidene-1-[(2'-(1H-tetrazole-5-yl)biphenyl-4yl)methyl]-4,5,6,7-tetrahydro-cycloheptimidazole (Compound 35)

(36) 2-Ethyl-8-(1-ethoxycarbonyloxy)ethoxycarbonylmethylidene-1-[(2'-(1H -tetrazole-5-yl)biphenyl-4yl)-methyl]-4,5,6,7-tetrahydro-cycloheptimidazole (Compound 36)

The compounds of the general formula (1) possess a potent angiotensin II receptor antagonist and they can be prepared by the following procedure.

(1) In case of

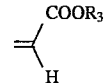

($R_3$=a lower alkyl group) is substituted at the 4 position in the compound of the general formula (1), these compouds are prepared according to the Scheme I.

Scheme I

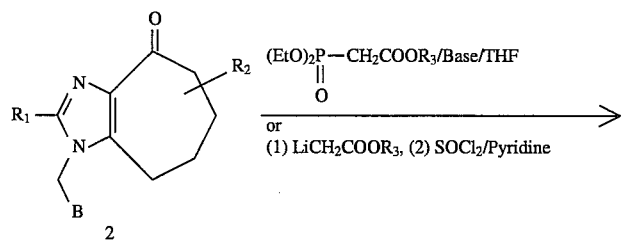

-continued
Scheme I

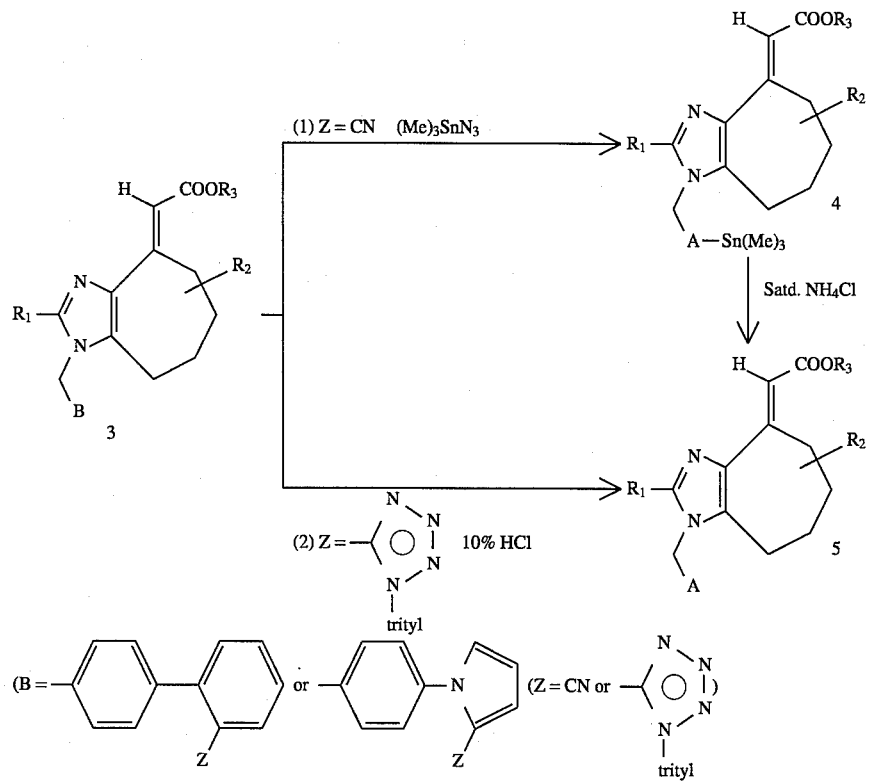

As used herein, base includes KH, NaH, NaOEt etc.

In case of $R_3$ is H, these compounds are prepared according to the Scheme II.

Scheme II

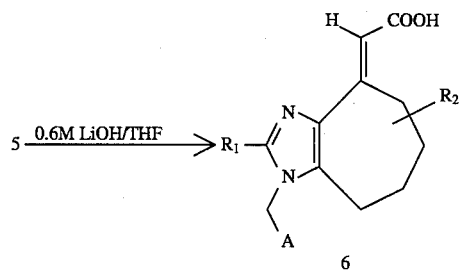

(2) In case of

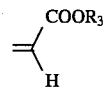

($R_3$ is a lower alkyl group) is substituted at the 8 position in the compound of the general formula (1), these compounds are prepared according to the Scheme III. The general formula 3 and 9 are obtained as trans isomers.

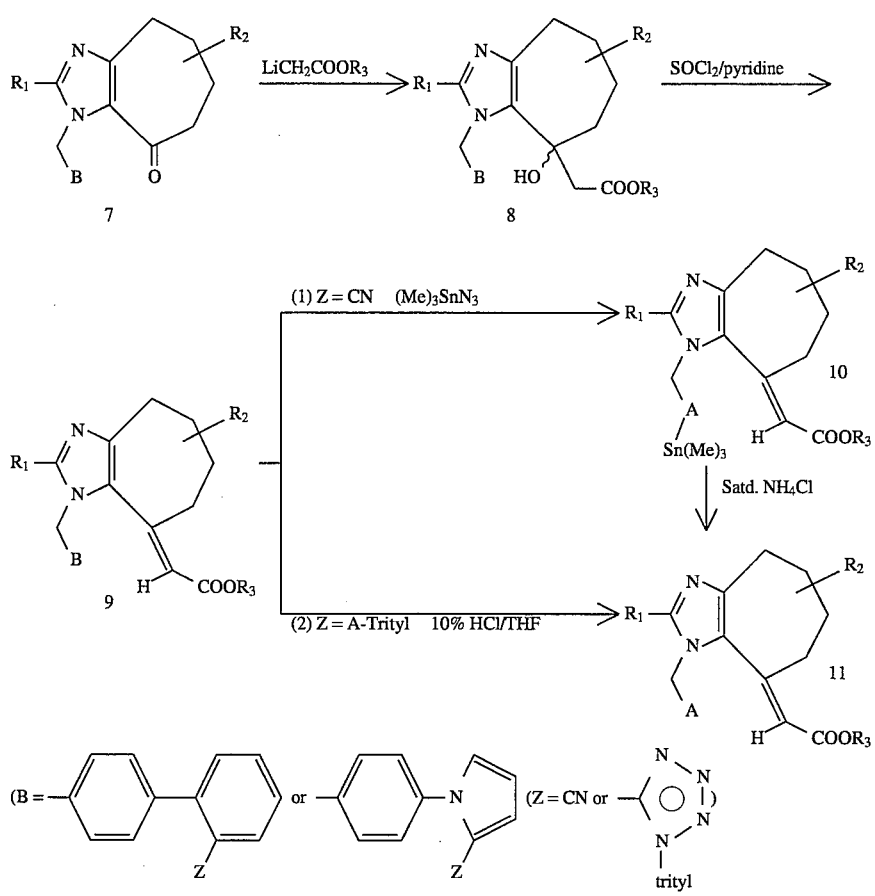
In case of $R_3$ is H, these compounds are prepared according to the Scheme IV.
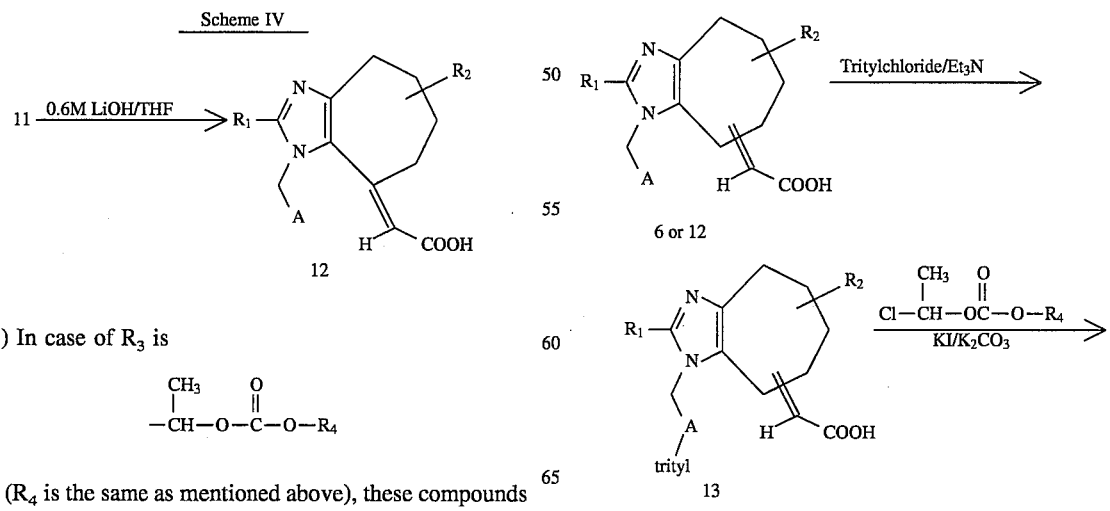
(3) In case of $R_3$ is
$$-\overset{CH_3}{\underset{|}{CH}}-O-\overset{O}{\underset{\|}{C}}-O-R_4$$
($R_4$ is the same as mentioned above), these compounds are prepared according to the Scheme V.

-continued
Scheme V

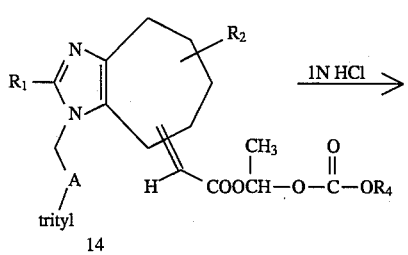

14

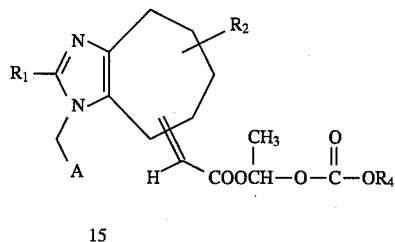

15

The compound of general formula 5 can be obtained from usual Homer-Emmons reaction of 4-oxo- 5,6,7,8-tetrahydro-cycloheptimidazole shown by the general formula 2 to give the compound of general formula 3, followed by detritylation and also obtained from the reaction of the general formula 2 with LiCH$_2$COOR$_3$ then SOCl$_2$/Pyridine (B. E. Evans et al. J. Med. Chem. 35, 3919–27 (1992)). LiCH$_2$COOR$_3$ is prepared according to the reported method (R. S. Old, ed. Modern Synthetic Method, Verlag, p. 8 (1992)).

The compounds of general formula 2 and 7 are prepared as follows. Tosyltropolone is reacted with suitable alkyl amidine to give 2-alkyl-4-oxo-cycloheptimidazole and 2-alkyl-8-oxo-cycloheptimidazole (J. Nakazawa et al. Ann. Sankyo Res. Lab. 21, 47 (1969)). Sequential catalytic hydrogenation of these compounds over Pd—C give 2-alkyl-4-oxo-5,6,7,8-tetrahydro-cycloheptimidazole and 2-alkyl-8-oxo-4,5,6,7-tetrahydro-cycloheptimidazole, followed by coupling with Br—CH$_2$—B (B=CN or A-Trityl) to give starting compounds. This manufacturing method is described in Japan Patent Application No 1992-131142.

In case of B is

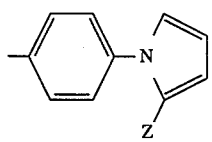

(Z is CN or

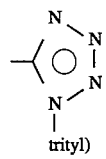

trityl)

in the compound of general formula 2, compound 21 is prepared according to the reported method (M. Artico et al., Farmaco Ed. Sc., 27, 60–7 (1972)).

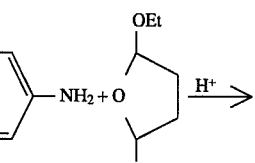

16    17

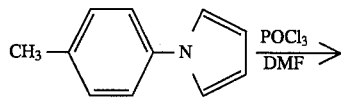

18

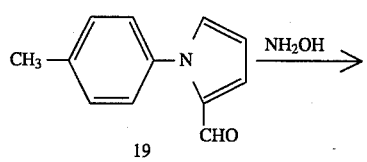

19

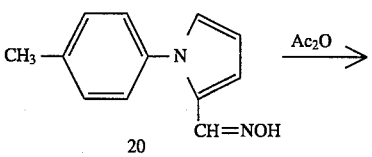

20

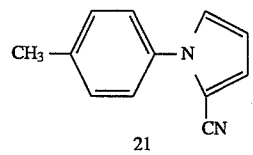

21

Obtained compound 21 is converted to compound 23 by the method of P. R. Bovy et al. (J. Med. Chem. 36, 101–110 (1993)) as follows.

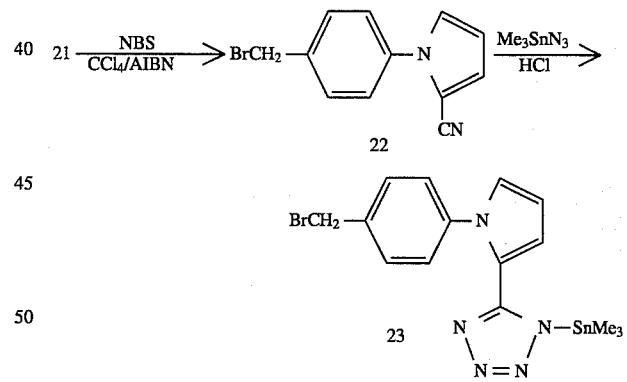

The compound of general formula 5 is obtained by the hydrolysis of compound 4 as shown in Scheme I.

The compound of general formula 9 is obtained by the reaction of the compound 7 with LiCH$_2$COOR$_3$ to give compound of the general formula 7, followed by the dehydration with SOCl$_2$/Pyridine to give the compound of the general formula 8, then the compound of general formula 8 is detritylated to give the compound of the general formula 9. The compound of general formula 11 is hydrolyzed to the compound of general formula 12 as shown in Scheme IV.

The compound of general formula 13 is obtained as shown in Scheme V. The compounds of general formula 6 or 12 are tritylated to give the compound of general formula 13, and which is reacted with

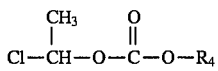

(R₄ is same as mentioned above) according to the method described in Japan Kokai Pat. 60-156688 to give the carbonate ester of general formula 14, then the compound of general formula 14 is detritylated to give the compound of general formula 15.

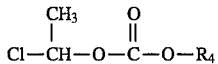

for this reaction is prepared according to the method described in the same patent as follows.

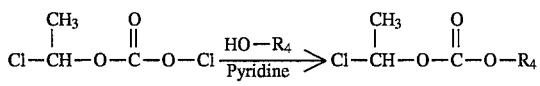

The compounds of formula (1) of the invention have an angiotensin II receptor antagonistic effect which will be explained later. They can be administered orally in the form of tablets, capsules, granules and syrups and also can be administered not orally such as direct administration rectally and in the form of injections. The pharmaceutically acceptable carriers are ethylcellulose, starch, lactose, etc.

An effective dosage of the compound is from 5 to 1000 mg once to several times a day for adults, though it may be adjusted depending on age and symptoms.

PHARMACOLOGICAL EXPERIMENT

[AII receptor antagonistic activity]

Angiotensin II receptor activity experiments are carried out according to P. C. Wong et al. (Hypertension 15, 823 (1990)).

Rabbit thoracic aorta is isolated, contracted by angiotensin II. The inhibition of contraction by the compound of formula (1) is expressed as $pA_2$ from dose-response curve (Schild, Brit. J. Pharmacol. 14, 48 (1959)) or expressed as $pD_2'$ according to the method of J. M. Van Rossum (Arch. Intern. Pharmacodyn., 143, 229 (1963)).

TABLE 1

| Compd. No | pA2 | Compd. No | pA2 |
|---|---|---|---|
| 2 | 7.44 | 22 | 8.90 |
| 3 | (9.00) | 23 | (9.60) |
| 4 | (8.40) | 24 | 9.80 |
| 14 | 9.80 | 25 | (8.88) |
| 15 | (9.91) | 26 | 9.30 |
| 16 | (9.91) | 27 | (8.45) |
| 17 | (9.86) | 29 | (8.18) |
| 18 | (9.03) | 30 | (8.11) |
| 19 | 8.82 | 32 | (9.38) |
| 20 | (9.04) | 35 | (8.12) |
| 21 | (9.08) | 36 | (8.59) | pD2' values are shown in parenthesis

[Inhibition of AII induced Blood Pressure Increase]

Carotid artery and left femoral vein in rats were cannulated. Next day, the carotid catheter was connected to a pressure transducer for monitoring arterial blood pressure. After the measurement of AII (30 ng/kg, i.v.) pressor responses, test compounds (0.3 mg/kg) were administered orally.

Thereafter, the pressor responses to AII at set times were measured and the inhibition percent was calculated according to the comparison of the pressor responses.

TABLE 2

| Compd. No | Inhibition | Compd. No | Inhibition |
|---|---|---|---|
| 4 | ++ | 28 | +++ |
| 7 | +++ | 29 | +++ |
| 16 | +++ | 31 | +++ |
| 17 | ++ | 33 | +++ |

+++ ≧ 70%, ++ < 70 ~≧ 50%, + 50 ~≧ 30%

REFERENCE

Reference 1: 2-propyl-4-oxo-5,6,7,8-tetrahydro-cycloheptimidazole.

A solution of 2-propyl-8-oxo-cycloheptimidazole (2.5 g) which was prepared by method of J. Nakazawa et al (Ann. Sankyo. Res. Lab., 1969, 21, 47) in THF (50 ml) and MeOH (20 ml) was stirred with 10% Pd—C (0.75 g) under $H_2$ atmosphere at room temperature. The catalyst was filtered off, and the solution was concentrated in vacuo. The resulting product was purified by silica gel column chromatography. Elution was carried out with ethyl acetate/methanol (10/1). The object compound was obtained as a colorless crystal: mp (°C.) 98–99.5; MS (m/e) 192 ($M^+$), 164 (BP); $^1$H-NMR (CDCl₃, ppm) δ0.97 (3H, t, J=7.4, —CH₂CH₂CH₃), 1.57–2.14 (6H, m, —CH₂CH₂CH₃, —CH₂CH₂—), 2.61–2.98 (6H, m, —CH₂CH₂CH₃, —CH₂CH₂).

Reference 2: 2-propyl-4-oxo-1-[(2'-(2-trityl-2H-tetrazole-5-yl)biphenyl-4-yl)methyl]-5,6,7,8-tetrahydro-cycloheptimidazole.

2-propyl-4-oxo-5,6,7,8-tetrahydro-cycloheptimidazole (3.5 g) which was prepared by reference 1 was dissolved in DMF (30 ml), sodium hydride (1.0 g, 55% in oil) was added, and the mixture was stirred at room temperature for 20 min. Then 1-trityl-5-(2-(4-bromomethylbiphenylyl))tetrazole (13.5 g) was added, and the mixture was stirred at room temperature for 5 hrs. The reaction mixture was concentrated in vacuo. After addition of ethyl acetate, the ethyl acetate layer was washed with brine, followed by a wash with dried (Na₂SO₄), filtered, and concentrated. The resulting product was purified by silica gel column chromatography in a usual way. Elution was carried out with ethyl acetate and subsequently crystallized from ethyl acetate. The object compound was obtained (3.5 g): mp (°C.) 189–190 (dec); $^1$H-NMR (CDCl₃, ppm) δ0.97 (3H, t, J=7.4 —CH₂CH₂CH₃), 1.56–2.10 (6H, m, —CH₂CH₂CH₃, —CH₂CH₂—), 2.40–2.90 (6H, m, —CH₂CH₂CH₃, —CH₂CH₂—), 4.93 (2H, S, —CH₂C₆H₅), 6.60–8.01 (23H, m, aromatic).

Reference 3: 2-methyl-8-oxo-4,5,6,7-tetrahydro-cycloheptimidazole.

A solution of 2-methyl-8-oxo-cycloheptimidazole (2.5 g) which was prepared by method of J. Nakazawa et al (Ann. Sankyo. Res. Lab., 1969, 21, 47) in THF (50 ml) and MeOH (20 ml) was stirred with 10% Pd-c (0.75 g) under $H_2$ atmosphere at room temperature. The catalyst was filtered off, and the solution was concentrated in vacuo. The resulting product was purified by silica gel column chromatography. Elution was carried out with ethyl acetate/methanol (10/1). The object compound was obtained as a colorless crystal: mp (°C.) 170.5–172; MS (m/e) 164 ($M^+$), 83 (BP); $^1$H-NMR (CDCl₃, ppm) δ1.73–2.16 (4H, m, —(CH₂)₂—), 2.43 (3H, S, CH₃), 2.59–3.08 (4H, m, —(CH₂)₂—).

Reference 4: 2-methyl-8-oxo-1-[(2'-carbonitryl)biphenyl-4-yl)methyl]- 4,5,6,7-tetrahydro-cycloheptimidazole.

2-methyl-8-oxo-4,5,6,7-tetrahydro-cycloheptimidazole (1.9 g) which was prepared by reference 3 was dissolved in toluene (70 ml). 30% NaOH aqueous solution (30 ml) was added and the mixture was stirred at room temperature for 30 min. 2'-carbonitryl-4-bromomethyl-biphenyl (3.94 g) and tetrabutyl-ammonium hydrogensulfate (0.79 g) were then added and the reaction mixture was stirred at 40° C. for 24 hrs. The solution was filtered, and the filtrate was extracted with toluene (50 ml×2), and the toluene layer was washed with water and then brine and dried with ($Na_2SO_4$), filtered, and concentrated in vacuo. The resulting product was purified by silica gel column chromatography. Elution was carried out with ethyl acetate/methanol (10/1). The object compound was obtained as a colorless crystal (3.1 g): mp (°C.) 101–103; MS (m/e) 355 ($M^+$), 192 (BP); 1H-NMR ($CDCl_3$, ppm) δ1.70–2.13 (4H, m, —$(CH_2)_2$—), 2.39 (3H, S, $CH_3$) 2.50–3.15 (4H, m, —$(CH_2)_2$—), 5.61 (2H, S, —C$\underline{H}_2C_6H_5$—), 6.95–7.80 (8H, m, aromatic).

EXAMPLE

Example 1

2-propyl-4-ethoxycarbonylmethylidene-1-[(2'-(1H-tetrazole-5-yl)biphenyl- 4-yl)methyl]-5,6,7,8-tetrahydro-cycloheptimidazole (compound 1).

(a) 2-propyl-4-ethoxycarbonylmethylidene-1-[(2'-(2-trityl-2H-tetrazole-5-yl)biphenyl-4-yl)methyl]-5,6,7,8-tetrahydro-cycloheptimidazole.

35% KH (0.5 ml) was washed by dry pentane under an argon atmosphere, and dry THF (10 ml) was added. Then diethyl phosphonoacetate (0.36 ml) was added, and the mixture was stirred at 10° C. for 10 min, and 2-propyl-4-oxo-1-[(2'-(2-trityl-2H-tetrazole-5-yl)biphenyl- 4-yl)methyl]-4,5,6,7-tetrahydro-cycloheptimidazole (0.3 g) which was prepared by reference 2 was added at 0° C. The mixture was stirred at room temperature for over night. The reaction mixture was quenched with saturated aqueous $NH_4Cl$ and extracted with ethyl acetate. The organic layer was washed with water and then brine and dried ($Na_2SO_4$), filtered, and concentrated in vacuo. The resulting product was purified by silica gel column chromatography. Elution was carried out with ethyl acetate/n-hexane (2/1) and subsequent crystallized from ethyl acetate. The object compound was obtained: mp (°C.) 189–191 (dec); 1H-NMR ($CDCl_3$, ppm) δ0.97 (3H, t, J=7.4, —$CH_2CH_2C\underline{H}_3$), 1.25 (3H, t, J=7.0, —COOC$H_2$C$\underline{H}_3$), 1.55–2.05 (6H, m, —$CH_2C\underline{H}_2CH_3$, —$C\underline{H}_2CH_2$—), 4.22 (2H, q, J=7.0, —COOC$\underline{H}_2CH_3$), 4.86 (2H, S, —C$\underline{H}_2C_6H_5$), 5.69 (1H, S,

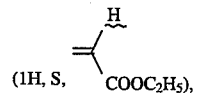

6.65–8.05 (23H, m, aromatic).

(b) 2-propyl-4-ethoxycarbonylmethylidene-1-[(2'-(1H-tetrazole-5-yl)biphenyl- 4-yl)methyl]-5,6,7,8-tetrahydro-cycloheptimidazole (compound 1).

2-propyl-4-ethoxycarbonylmethylidene-1-[(2'-(2-tritil-2H-tetrazole-5-yl)biphenyl-4-yl)methyl]-5,6,7,8-tetrahydro-cycloheptimidazole (0.18 g) which was prepared by method (a) of example 1 was dissolved in MeOH (3 ml), 10% HCl (0.5 ml) was added, and the mixture was stirred at room temperature for 4 hrs. After treating with 10% NaOH to adjust the pH 4.0–4.5, the solution was extracted with chloroform, and the chloroform layer was concentrated. The resulting product was purified by silica gel column chromatography in the usual manner. Elution was carried out with chloroform/methanol (10/1) and subsequently crystallized from isopropylalcohol. The object compound was obtained as a white crystal (0.11 g): mp (°C.) 112–113; MS (m/e) 496 ($M^+$), 169 (BP); IR (KBr, $cm^{-1}$) 3420, 2920, 1704, 1176, 770; 1H-NMR ($CDCl_3$, ppm) δ0.90 (3H, t, J=7.4, —$(CH_2)_2C\underline{H}_3$), 1.22 (3H, t, J=7.0, —$CO_2CH_2C\underline{H}_3$), 1.52–2.15 (6H, m, —CHC$\underline{H}_2CH_3$, —C$\underline{H}_2CH_2$—), 2.30–3.20 (6H, m, —C$\underline{H}_2CH_2CH_3$, —C$\underline{H}_2CH_2$—), 4.17 (2H, q, J=7.0, —$CO_2C\underline{H}_2CH_3$), 5.39 (2H, S, —C$\underline{H}_2C_6H_5$), 5.83

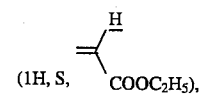

6.40–7.85 (8H, m, aromatic),

Example 2

2-methyl-8-ethoxycarbonylmethylidene-1-[(2'-(1H-tetrazole-5-yl)biphenyl- 4-yl)methyl]-4,5,6,7-tetrahydro-cycloheptimidazole (compound 2).

(a) 2-methyl-8-ethoxycarbonylmethyl-8-hydroxy-1-[(2'-carbonitryl)biphenyl-4-yl)methyl]- 4,5,6,7-tetrahydro-cycloheptimidazole.

To a solution of 1.0M $(Me_3Si)_2NLi$ in THF (18.6 ml) was added a dry ethyl acetate (1.74 ml) at −78° C., and the mixture was stirred for 30 min. Then 2-methyl-8-oxo-1-[(2'-carbonitryl)biphenyl-4-yl)methyl]-4,5,6,7-tetrahydro-cycloheptimidazole (3.1 g) which was prepared by reference 4 in 25 ml of dry THF was dropwised over 1 hr. The reaction mixture was stirred at −78° C. for 1.5 hrs, and treated with 6N HCl (6 ml) to adjust the pH 5.0. The reaction mixture was extracted with ethyl acetate. The ethyl acetate layer was washed with water and then brine and dried ($Na_2SO_4$), filtered, and concentrated in vacuo. The resulting product was purified by silica gel column chromatography. Elution was carried out with ethyl acetate/methanol (10/1). The object compound was obtained as an oil (0.53 g): MS (m/e) 443 ($M^+$), 190 (BP); IR (KBr, $cm^{-1}$) 2920, 2250, 1728, 1410, 1368, 753; 1H-NMR ($CDCl_3$, ppm) δ1.24 (3H, t, J=7.0, —COOC$H_2C\underline{H}_3$), 1.55–2.95 (10H, m, —(C$\underline{H}_2)_4$—+—$CH_2$COOEt), 3.28–3.87 (1H, bs, OH), 3.87–4.33 (2H, t, J=7.0, —COOC$\underline{H}_2CH_3$), 5.59 (2H, q, —C$\underline{H}_2C_6H_5$), 6.90–7.80 (8H, m, aromatic).

(b) 2-methyl-8-ethoxycarbonylmethylidene-1-[(2'-carbonitryl)biphenyl-4-yl)methyl]- 4,5,6,7-tetrahydro-cycloheptimidazole.

2-methyl-8-ethoxycarbonylmethyl-8-hydroxy-1-[(2'-carbonitryl)biphenyl-4-yl)methyl]-4,5,6,7-tetrahydro-cycloheptimidazole (0.53 g) which was prepared by method (a) of example 2 was dissolved in pyridine (2 ml), $SOCl_2$ (0.26 ml) was added, and the mixture was stirred at room temperature for 30 min. The reaction mixture was poured into 10% HCl (10 ml) at 0° C., and extracted with ethyl acetate, and ethyl acetate layer was washed with brine and dried ($Na_{2SO4}$), filtered, and concentrated in vacuo. The resulting product was purified was silica gel column chromatography. Elution was carried out with ethyl acetate. The object compound was obtained as an oil (0.3 g): MS (m/e) 426 ($M^+$+1), 192 (BP); IR (KBr, $cm^{-1}$) 2920, 2250, 1704, 1617, 1476, 1446, 1413, 1170, 753; 1H-NMR ($CDCl_3$, ppm) δ1.24 (3H, t, J=7.14, —CH$_2$CH$_3$), 1.68–2.00 (4H, m, —(CH$_2$)$_2$—), 2.32 (3H, S, CH$_3$), 2.65–3.21 (4H, m, —(CH$_2$)$_2$—), 4.12 (2H, q, —CH$_2$CH$_3$), 5.22 (2H, S, —CH$_2$C$_6$H$_5$), 5.56

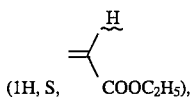

(1H, S, COOC$_2$H$_5$), 6.92–7.83 (8H, m, aromatic).

(c) 2-methyl-8-ethoxycarbonylmethylidene-1-[(2'-(1H-tetrazole-5-yl)biphenyl- 4-yl)methyl]-4,5,6,7-tetrahydro-cycloheptimidazole (compound 2).

2-methyl-8-ethoxycarbonylmethylidene-1-[(2'-carbonitryl)biphenyl-4-yl)methyl]-4,5,6,7-tetrahydro-cycloheptimidazole (0.3 g) which was prepared by method (b) of example 2 was dissolved in toluene (25 ml), trimethyltin azide (0.57 g) was added, and the mixture was refluxed for 2 days. The reaction mixture was poured into saturated NH$_4$Cl (25 ml) and extracted with chloroform, and the chloroform layer was washed with brine and dried (Na$_2$SO$_4$), filtered, and concentrated in vacuo. The resulting product was purified was silica gel column chromatography. Elution was carried out with chloroform/methanol (50/1). The compound 2 was obtained as a colorless crystal (0.18 g): mp (°C.) 157.5–159.5; MS (m/e) 469 (M$^+$+1), 192 (BP); IR (KBr, cm$^{-1}$) 2920, 1704, 1620, 1449, 1410, 1173; $^1$H-NMR (CDCl$_3$, ppm) δ1.18 (3H, t, J=7.0, —CH$_2$CH$_3$), 1.35–2.25 (6H, m, —(CH$_2$)$_3$—), 2.02 (3H, S, CH$_3$), 2.70–3.05 (2H, m, —CH$_2$—), 4.07 (2H, q, J=7.0, —CH$_2$CH$_3$), 5.09 (2H, S, —CH$_2$C$_6$H$_5$), 5.40

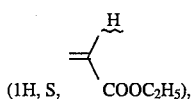

(1H, S, COOC$_2$H$_5$), 6.57–7.90 (8H, m, aromatic), 11.55 (1H, bs, NH).

Example 3–13

(Compound 3–13)

Compound 3–13 were prepared in a similar manner as described in Example 2.

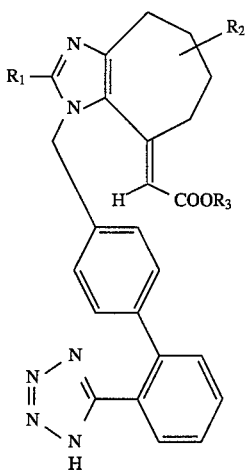

A

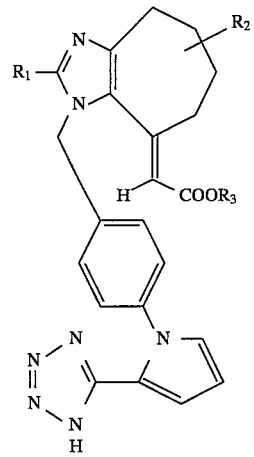

B

TABLE 3

| Example | Compd. No. | Structural Formula | R$_1$ | R$_2$ | R$_3$ | mp (°C.) |
|---|---|---|---|---|---|---|
| 3 | 3 | A | C$_2$H$_5$ | H | C$_2$H$_5$ | 118.5–120 |
| 4 | 4 | A | C$_3$H$_7$ | H | C$_2$H$_5$ | 115–118 |
| 5 | 5 | A | C$_4$H$_9$ | H | C$_2$H$_5$ | 210–212 |
| 6 | 6 | A | C$_5$H$_{11}$ | H | C$_2$H$_5$ | 199–201 |
| 7 | 7 | A | C$_2$H$_5$ | 6-i-Pro | C$_2$H$_5$ | 134–136 |
| 8 | 8 | A | C$_3$H$_7$ | 6-i-Pro | C$_2$H$_5$ | 127–129 |
| 9 | 9 | B | CH$_3$ | H | C$_2$H$_5$ | 101–103 |
| 10 | 10 | B | C$_2$H$_5$ | H | C$_2$H$_5$ | 122–123 |
| 11 | 11 | B | C$_3$H$_7$ | H | C$_2$H$_5$ | 168–169 |
| 12 | 12 | A | C$_4$H$_9$ | 6-i-Pro | C$_2$H$_5$ | 114–115 |
| 13 | 13 | B | C$_4$H$_9$ | H | C$_2$H$_5$ | 176–178 |

Example 14

2-propyl-4-carboxymethylidene-1-[(2'-(1H-tetrazole-5-yl)biphenyl-4-yl)methyl]-5,6,7,8-tetrahydro-cycloheptimidazole (compound 14).

2-propyl-4-ethoxycarbonylmethylidene-1-[(2'-(1H-tetrazole-5-yl)biphenyl-4-yl)methyl]-5,6,7,8-tetrahydro-cycloheptimidazole (compound 1) (60 mg) which was prepared by method of example 1 was dissolved in MeOH (1 ml), and 0.6N LiOH aqueous solution (3 ml) was added, and the mixture was stirred at 50% for 6 hrs. The aqueous solution was treated with 10% HCl dropwise to adjust the pH 4.0. The mixture was extracted with chloroform, and the chloroform layer was washed with brine and dried with (Na$_2$SO$_4$), filtered, and concentrated in vacuo. The resulting product was recrystallized with EtOH. The product was obtained as a colorless crystal (40 mg): mp (°C.) 168–170; MS (m/e) 424 (M$^+$—COOH); IR (KBr, cm$^{-1}$) 2940, 1670, 1470, 1375, 1251, 880; $^1$H-NMR (CDCl$_3$, ppm) δ0.95 (3H, t, —CH$_2$CH$_2$CH$_3$), 1.40–2.90 (6H, m, —CH$_2$CH$_2$CH$_3$, —(CH$_2$)$_2$), 2.10–2.90 (6H, m, —CH$_2$CH$_2$CH$_3$, —(CH$_2$)$_2$—), 5.03 (2H, S, —CH$_2$C$_6$H$_5$), 5.66

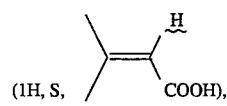

(1H, S, COOH), 16.40–7.80 (8H, m, aromatic).

Example 15

2-methyl-8-carboxymethylidene-1-[(2'-(1H-tetrazole-5-yl)biphenyl-4-yl)methyl]-4,5,6,7-tetrahydro-cycloheptimidazole (compound 15).

2-methyl-8-ethoxycarbonylmethylidene-1-[(2'-(1H-tetrazole-5-yl)biphenyl-4-yl)methyl]-4,5,6,7-tetrahydro-cycloheptimidazole (compound 2) (0.1 g) which was prepared by method of example 2 was dissolved in THF (2 ml), and 0.6N LiOH aqueous solution (2.1 ml) was added, and the mixture was stirred at 50° C. for over night. The aqueous solution was treated with 10% HCl dropwise to adjust the pH 4.0. The resulting precipitate was collected by filtration, and was recrystallized with isopropyl alcohol. The product was obtained as a colorless crystal (0.04 g): mp (°C.) 172–174; MS (m/e) 396 ($M^+$—COOH), 192 (BP); IR (KBr, $cm^{-1}$) 2920, 2650, 2554, 1704, 1644, 1611, 1443, 1389, 1362, 1314, 1227, 1197, 1155, 753; $^1$H-NMR ($CD_3OD$, ppm) δ1.91 (4H, bs, —$(CH_2)_2$—), 2.48 (3H, S, $CH_3$), 2.60–3.04 (4H, m, —$(CH_2)_2$—), 5.40 (2H, S, —$C\underline{H}_2C_6H_5$), 5.90

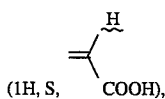

(1H, S, COOH), 6.82–7.68 (8H, m, aromatic), 7.94 (1H, S, NH).

Example 16–26

Compound 16–26 were prepared in a similar manner as described in Example 15.

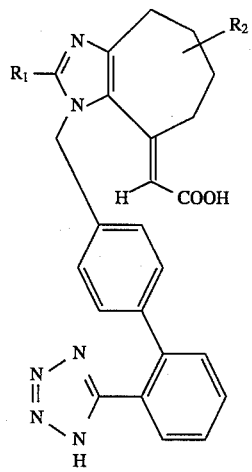

A

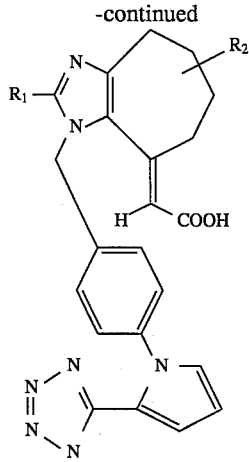

B

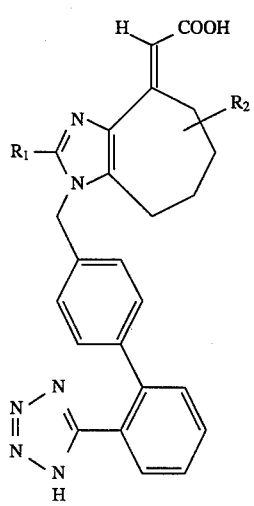

C

TABLE 4

| Example | Compd. No. | Structural Formula | $R_1$ | $R_2$ | mp (°C.) |
|---------|-----------|--------------------|-------|-------|----------|
| 14 | 14 | C | $C_3H_7$ | H | 168–170 |
| 15 | 15 | A | $CH_3$ | H | 172–174 |
| 16 | 16 | A | $C_2H_5$ | H | 191–193 |
| 17 | 17 | A | $C_3H_7$ | H | 128–130 |
| 18 | 18 | A | $C_4H_9$ | H | 239–241 |
| 19 | 19 | A | $C_5H_{11}$ | H | 228–230 |
| 20 | 20 | A | $C_2H_5$ | 6-i-Pro | 203–205 |
| 21 | 21 | A | $C_3H_7$ | 6-i-Pro | 199–201 |
| 22 | 22 | B | $CH_3$ | H | 204–206 |
| 23 | 23 | B | $C_2H_5$ | H | 229–230 |

TABLE 4-continued

| Example | Compd. No. | Structural Formula | $R_1$ | $R_2$ | mp (°C.) |
|---|---|---|---|---|---|
| 24 | 24 | B | $C_3H_7$ | H | 232–233 |
| 25 | 25 | A | $C_4H_9$ | 6-i-Pro | 134–136 |
| 26 | 26 | B | $C_4H_9$ | H | 225 (dec) |

Example 27

2-propyl-8-(1-ethoxycarbonyloxy)-ethoxycarbonylmethylidene-1-[(2'-(1H-tetrazole-5-yl)biphenyl-4-yl)methyl]-4,5,6,7-tetrahydro-cycloheptimidazole (compound 27).

(a) 2-propyl-8-carboxymethylidene-1-[(2'-(2-triphenylmethyl-2H-tetrazole-5-yl)biphenyl-4-yl)methyl]-4,5,6,7-tetrahydro-cycloheptimidazole.

2-propyl-8-carboxymethylidene-1-[(2'-(1H-tetrazole-5-yl)biphenyl-4-yl)methyl]-4,5,6,7-tetrahydro-cycloheptimidazole (compound 17) (1.6 g) was dissolved in $CH_2Cl_2$ (100 ml), and triethylamine (0.27 ml) was added. Then triphenylmethylchloride (1.1 g) was added, and the mixture was stirred at room temperature for over night. The reaction mixture was extracted with chloroform. The organic layer was washed with water and then brine and dried with ($Na_2SO_4$), filtered, and concentrated in vacuo. The resulting product was purified by silica gel column chromatography. Elution was carried out with chloroform/methanol (20/1). The object compound was obtained as a pale yellow oil (2.0 g): $^1$H-NMR ($CDCl_3$, ppm) δ0.81 (3H, t, $C_2H_5$—C$\underline{H}_3$), 1.34–3.20 (12H, m, —$(CH_2)_6$—), 5.05 (2H, S, —C$\underline{H}_2C_6H_5$), 5.50

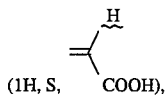

(1H, S, COOH), 6.35–7.95 (23H, m, aromatic), 9.01–9.60 (1H, broad, COO$\underline{H}$).

(b) 2-propyl-8-(1-ethoxycarbonyloxy)ethoxycarbonylmethylidene-1-[(2'-(2-triphenylmethyl-2H-tetrazole-5-yl)biphenyl-4-yl)methyl]-4,5,6,7-tetrahydro-cycloheptimidazole.

2-propyl-8-carboxymethylidene-1-[(2'-(2-triphenylmethyl-2H-tetrazole-5-yl)biphenyl-4-yl)methyl]-4,5,6,7-tetrahydro-cycloheptimidazole (0.17 g) which was prepared by method (a) of example 27 and 1-(ethoxycarbonyloxy)ethylchloride (0.72 g) were dissolved in acetone (50 ml), potassium carbonate (0.66 g) and sodium iodide (0.72 g) was added. The reaction mixture was refluxed for 6 hrs and concentrated in vacuo. After addition of ethyl acetate (10 ml), the mixture was washed with brine, dried with ($Na_2SO_4$), filtered, and concentrated. The resulting product was purified by silica gel column chromatography in usually way. Elution was carried out with chloroform/methanol (10/1).

The object compound was obtained as a colorless oil (0.11 g): $^1$H-NMR ($CDCl_3$, ppm) δ0.86 (3H, t, —$C_2H_5C\underline{H}_3$) 1.24 (3H, t, —OCHC$\underline{H}_3$), 1.41

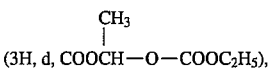

(3H, d, COOC$\underline{H}$—O—$COOC_2H_5$), 1.42–3.20 (12H, m, —$(CH_2)_6$—), 4.15 (2H, q, —OC$\underline{H}_2CH_3$), 5.20 (2H, S, —C$\underline{H}_2C_6H_5$), 5.45

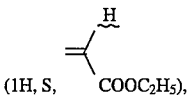

(1H, S, COOC$_2H_5$), 6.20–8.21 (24H, m, aromatic,

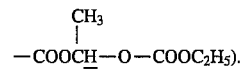

—COOC$\underline{H}$—O—$COOC_2H_5$).

(c) 2-propyl-8-(1-ethoxycarbonyloxy)-ethoxycarbonylmethylidene-1-[(2'-(1H-tetrazole-5-yl)biphenyl-4-yl)methyl]-4,5,6,7-tetrahydro-cycloheptimidazole. (compound 27).

2-propyl-8-(1-ethoxycarbonyloxy)-ethoxycarbonylmethylidene-1-[(2'-(2-triphenylmethyl-2H-tetrazole-5-yl)biphenyl-4-yl)methyl]-4,5,6,7-tetrahydro-cycloheptimidazole (0.11 g) which was prepared by method (b) of example 27 was dissolved in methanol (3 ml). 1N HCl (0.3 ml) was added and the mixture was stirred at room temperature for 2 hrs and poured into ice-water. The reaction mixture was extracted with chloroform. The chloroform layer was washed with water and then brine and dried with ($Na_2SO_4$), and concentrated in vacuo. The resulting product was purified by silica gel column chromatography. Elution was carried out with chloroform/methanol (20/1) and subsequent crystallized from methanol and ether.

The object compound was obtained as a colorless crystal (0.055 g): mp (°C.) 79–82 (dec); MS (m/e) 494 ($M^+$—$OCOC_2H_5$), 165 (BP); IR (KBr, $cm^{-1}$) 2720, 1750, 1611, 1452, 1371, 1263, 1146, 1071; $^1$H-NMR ($CDCl_3$, ppm) δ0.86 (3H, t, —$C_2H_5$), 1.26 (3H, t, —$CH_2C\underline{H}_3$), 1.42

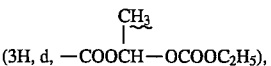

(3H, d, —COOC$\underline{H}$—$OCOOC_2H_5$), 1.43–3.20 (12H, m, —$(CH_2)_6$—), 4.15 (2H, q, —OC$\underline{H}_2CH_3$), 5.05 (2H, S, —C$\underline{H}_2C_6H_5$), 5.35

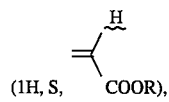

(1H, S, COOR), 6.40–8.00

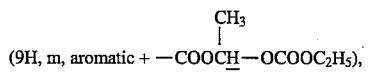

(9H, m, aromatic + —COOC$\underline{H}$—$OCOOC_2H_5$), 8.80–9.60 (1H, broad, NH).

Example 28–36

Compounds 28–36 were prepared in a similar manner as described in Example 27.

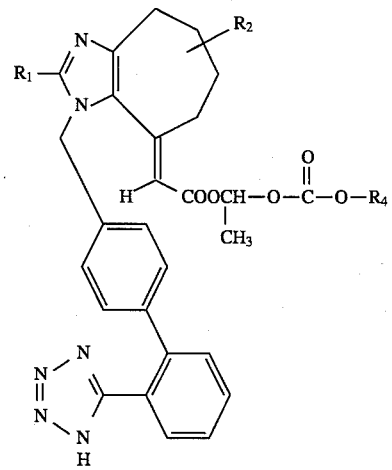

A

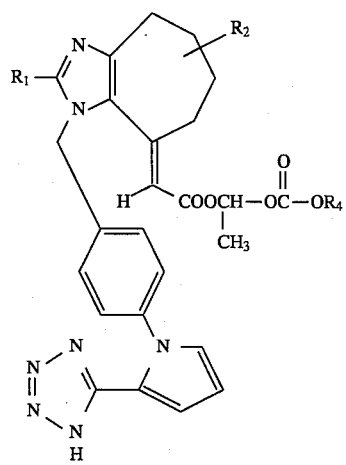

B

TABLE 5

| Example | Compd. No | Structural Formula | $R_1$ | $R_2$ | $R_4$ | mp (°C.) |
|---|---|---|---|---|---|---|
| 28 | 28 | A | $C_3H_7$ | H | cyclohexyl | 102–105 (dec) |
| 29 | 29 | A | $C_3H_7$ | H | isopropyl | 81–83 (dec) |
| 30 | 30 | A | $C_2H_5$ | H | isopropyl | 95 (dec) |
| 31 | 31 | A | $C_2H_5$ | 6-i-Pro | isopropyl | 129–130 (dec) |
| 32 | 32 | B | $C_2H_5$ | H | isopropyl | 110–111 (dec) |
| 33 | 33 | A | $C_3H_7$ | 6-i-Pro | isopropyl | 162–164 (dec) |
| 34 | 34 | A | $C_4H_9$ | 6-i-Pro | isopropyl | 87–89 (dec) |

TABLE 5-continued

| Example | Compd. No | Structural Formula | $R_1$ | $R_2$ | $R_4$ | mp (°C.) |
|---|---|---|---|---|---|---|
| 35 | 35 | A | $C_2H_5$ | H | cyclohexyl | 80 (dec) |
| 36 | 36 | A | $C_2H_5$ | H | propyl | 78 (dec) |

We claim:

1. A compound of general formula (1)

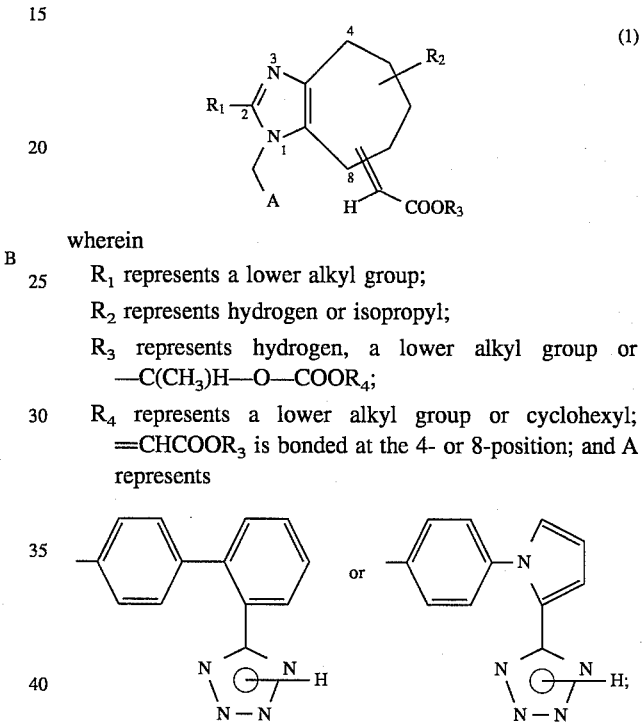

wherein $R_1$ represents a lower alkyl group;

$R_2$ represents hydrogen or isopropyl;

$R_3$ represents hydrogen, a lower alkyl group or —C(CH$_3$)H—O—COOR$_4$;

$R_4$ represents a lower alkyl group or cyclohexyl;

=CHCOOR$_3$ is bonded at the 4- or 8-position; and A represents or a salt thereof.

2. A method for preparing a compound of formula (1) as set forth in claim 1 wherein $R_3$ represents said lower alkyl group, said method comprising reacting a compound of general formula (a)

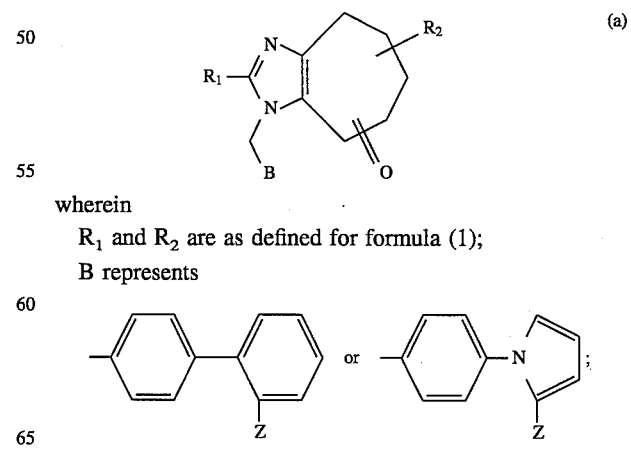

wherein $R_1$ and $R_2$ are as defined for formula (1);

B represents

Z represents CN or

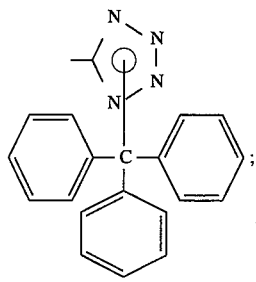

and oxo (=o) is bonded at the 4- or 8-position, with $LiCH_2COOR_3$, wherein $R_3$ represents said lower alkyl group, and dehydroxylating the resulting product with $SOCl_2$ to form a compound of general formula (b)

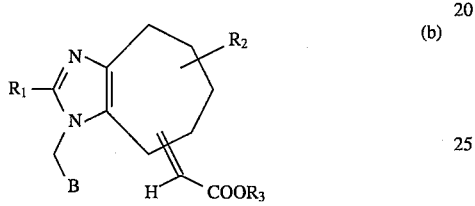

where $R_1$, $R_2$, $R_3$ and B are defined above and =CHCOOR$_3$ is bonded at the 4- or 8-position; and when Z represents CN reacting the compound of formula (b) with $(CH_3)_3SnN_3$, followed by detrimethyltinating the resulting product to produce the compound of formula (1), and when Z represents trityltetrazole, detritylating the compound of formula (b) to produce the compound of formula (1).

3. A method for preparing a compound of formula (1) as set forth in claim 1 wherein =CHCOOR$_3$ is bonded at the 4-position and $R_3$ represents said lower alkyl group, said method comprising reacting a compound of general formula (2)

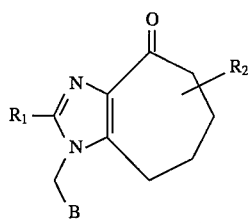

wherein $R_1$ and $R_2$ are as defined for formula (1) and B represents

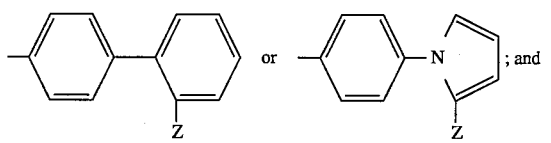

and

Z represents CN or trityltetrazole of formula

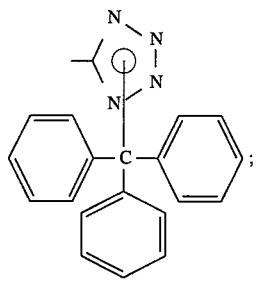

with $(C_2H_5O)_2P(O)CH_2COOR_3$, where $R_3$ represents said lower alkyl group, in the presence of a base to produce the compound of formula (3)

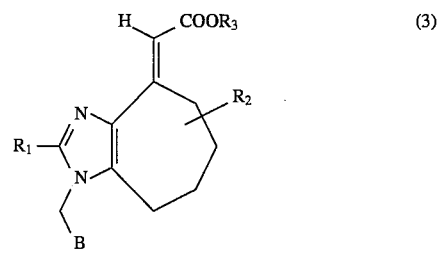

Wherein $R_1$, $R_2$, $R_3$ and B are as defined above; and when Z represents CN, reacting the compound of formula (3) with $(CH_3)_3SnN_3$ followed by detrimethyltinating the resulting product to produce the compound of formula (1); and when Z represents the trityltetrazole group, detritylating the compound of formula (3) to produce the compound of formula (1).

4. A pharmaceutical composition useful as an angiotensin II receptor antagonist comprising a therapeutically effective amount of a compound of general formula (1) as defined in claim 1 or a pharmaceutically acceptable salt thereof and a pharmaceutically acceptable carrier.

5. A method for treating hypertension in a patient in need thereof comprising administering to said patient a therapeutically effective amount of a compound of general formula (1) as set forth in claim 1.

6. A method for treating congestive heart failure in a patient in need thereof comprising administering to said patient a therapeutically effective amount of a compound as set forth in claim 1.

7. A method for lowering intraocular pressure in a patient in need thereof comprising administering to said patient a therapeutically effective amount of a compound as claimed in claim 1.

8. The compound of claim 1 wherein =CHCOOR$_3$ is bonded at the 4-position.

9. The compound of claim 1 wherein =CHCOOR$_3$ is bonded at the 8-position.

10. The compound of claim 8 wherein $R_3$ is hydrogen.

11. The compound of claim 8 wherein $R_3$ is a lower alkyl group.

12. The compound of claim 8 wherein $R_3$ is —C(CH$_3$)H—O—COOR$_4$.

13. The compound of claim 9 wherein $R_3$ is hydrogen.

14. The compound of claim 9 wherein $R_3$ is a lower alkyl group.

15. The compound of claim 9 wherein $R_3$ is —C(CH$_3$)H—O—COOR$_4$.

16. The compound of claim 1 wherein A represents

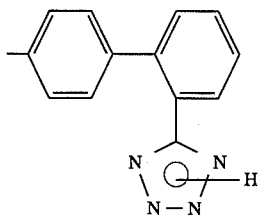

17. The compound of claim 1 wherein A represents

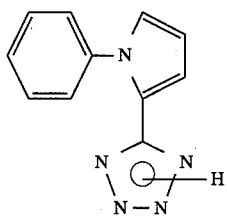

18. The compound of claim 1 wherein $R_1$ is an ethyl group, $R_2$ is hydrogen, $R_3$ is an ethyl group and =CHCOOR$_3$ is bonded at the 8-position.

19. A compound of general formula (1')

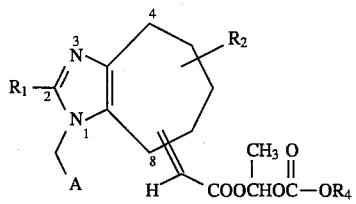

wherein $R_1$ represents a lower alkyl group;

$R_2$ represents hydrogen or isopropyl;

$R_4$ represents a lower alkyl group or cyclohexyl;

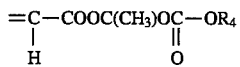

is bonded at the 4- or 8-position; and

A represents

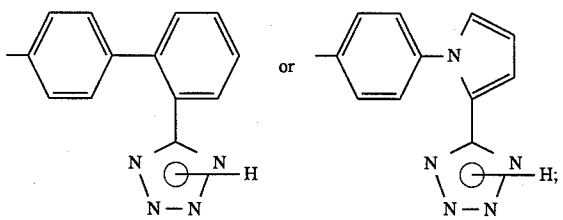

or a salt thereof.

20. A method for preparing a compound of formula (1) as set forth in claim 1 wherein $R_3$ represents hydrogen, said method comprising reacting a compound of general formula (a)

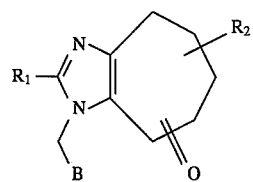

wherein $R_1$ and $R_2$ are as defined for formula (1);

B represents

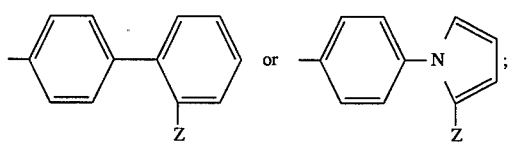

Z represents CN or

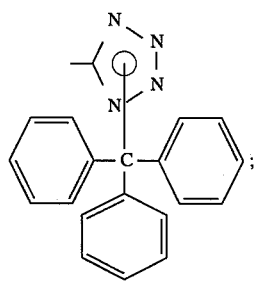

and oxo (=O) is bonded at the 4- or 8-position, with LiCH$_2$COOR$_3$, wherein $R_3$ represents said lower alkyl group, and dehydroxylating the resulting product with SOCl$_2$ to form a compound of general formula (b)

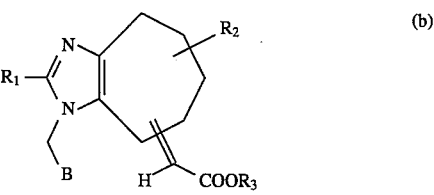

where $R_1$, $R_2$, $R_3$ and B are defined above and =CHCOOR$_3$ is bonded at the 4- or 8-position; and when Z represents CN reacting the compound of formula (b) with (CH$_3$)$_3$SnN$_3$, followed by detrimethyltinating the resulting product to produce the compound of formula (1) in which $R_3$ represents the lower alkyl group, or when Z represents trityltetrazole, detritylating the compound of formula (b) to produce the compound of formula (1) wherein $R_3$ represents the lower alkyl group; and hydrolyzing the compound of formula (1) wherein $R_3$ represents the lower alkyl group to thereby produce the compound of formula (1) wherein $R_3$ represents hydrogen.

21. The method of claim 20 wherein the step of hydrolyzing the compound of formula (1) wherein $R_3$ represents said lower alkyl group comprises reacting the compound of formula (1) wherein $R_3$ represents the lower alkyl group with lithium hydroxide.

22. A method for preparing a compound of formula (1)

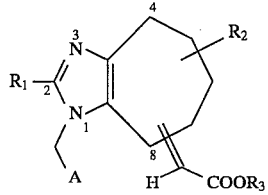

(1)

wherein $R_1$ represents a lower alkyl group;

$R_2$ represents hydrogen or isopropyl;

$R_3$ represents said —CH—O—COOR$_4$;

$R_4$ represents a lower alkyl group or cyclohexyl;

=CHCOOR$_3$ is bonded at the 4- or 8-position; and

A represents

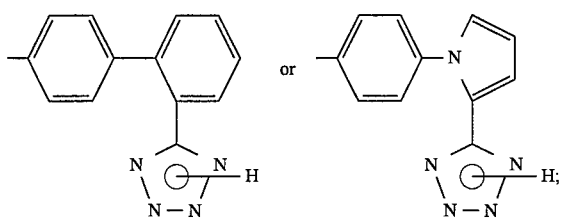

said method comprising protecting a compound of general formula (1) wherein $R_3$ represents a hydrogen atom with a trityl group, reacting the resulting protected compound with Cl—CH—O—COOR$_4$, and then detritylating the resulting compound to produce the compound of formula (1')

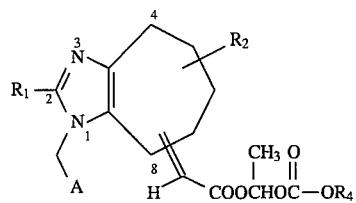

(1')

wherein $R_1$, $R_2$, $R_4$ and A are as defined and =CHCOOC(CH$_3$)HOCOOR$_4$ is bonded at the 4- or 8-position.

* * * * *